United States Patent [19]

Cooper et al.

[11] Patent Number: 5,051,823
[45] Date of Patent: Sep. 24, 1991

[54] DENTAL INSTRUMENT INCLUDING LASER DEVICE AND ELECTRONIC VIDEO DENTAL CAMERA

[75] Inventors: David H. Cooper, Saratoga; Charles S. Bush, Los Gatos, both of Calif.

[73] Assignee: Fuji Optical Systems, Inc., Los Gatos, Calif.

[21] Appl. No.: 467,517

[22] Filed: Jan. 18, 1990

Related U.S. Application Data

[63] Continuation-in-part of Ser. No. 149,521, Jan. 28, 1988, abandoned, which is a continuation-in-part of Ser. No. 22,171, Mar. 5, 1987, Pat. No. 4,727,416.

[51] Int. Cl.$^5$ .......................... A61B 1/04; A61B 1/06
[52] U.S. Cl. ......................................... 358/98; 128/6; 433/29; 433/31
[58] Field of Search ................ 358/98; 128/6; 433/29, 433/30, 31

[56] References Cited

U.S. PATENT DOCUMENTS

| | | |
|---|---|---|
| D. 267,745 | 1/1883 | Seeley . |
| D. 269,122 | 5/1983 | Seeley . |
| 3,051,166 | 8/1962 | Hovnanian . |
| 3,382,781 | 5/1968 | Hamilton ........................... 354/62 |
| 3,557,780 | 1/1971 | Sato . |
| 3,622,785 | 11/1971 | Irwin et al. ........................ 378/99 |
| 3,884,222 | 5/1975 | Moore ................................ 433/31 |
| 3,903,877 | 9/1975 | Terada . |
| 4,074,306 | 2/1978 | Kaminuma . |
| 4,260,376 | 4/1981 | Litel ................................... 358/93 |
| 4,273,535 | 6/1981 | Yamamoto ........................ 433/25 |
| 4,326,846 | 4/1982 | Sugai . |
| 4,330,281 | 5/1982 | Hayashi . |
| 4,355,977 | 10/1982 | Ota . |

(List continued on next page.)

FOREIGN PATENT DOCUMENTS

| | | |
|---|---|---|
| 0073617 | 3/1983 | European Pat. Off. . |
| 0122537A1 | 10/1984 | European Pat. Off. . |
| 0184778A3 | 6/1986 | European Pat. Off. . |
| 0280823 | 9/1988 | European Pat. Off. . |
| 296520 | 12/1988 | European Pat. Off. . |
| 2208902 | 8/1973 | Fed. Rep. of Germany . |
| DE2308554 | 8/1974 | Fed. Rep. of Germany . |
| 2505 | 8/1976 | Fed. Rep. of Germany . |
| DE3045162 | 1/1982 | Fed. Rep. of Germany . |
| DE32334-10A1 | 4/1984 | Fed. Rep. of Germany . |
| 53-45081 | 4/1978 | Japan . |
| 922994 | 4/1963 | United Kingdom . |

OTHER PUBLICATIONS

Toshiba et al., "Ultracompact CCD Color Television Camera," *Toshiba Review*, No. 158, Winter 1986.
Myers et al., "A Review of Lasers in Dentistry," *II Dentista Moderno* (1989).
Myers et al., "The Use of a Laser for Debridement or
(List continued on next page.)

*Primary Examiner*—Howard W. Britton
*Attorney, Agent, or Firm*—Steven F. Caserza

[57] ABSTRACT

A novel dental instrument is taught which includes both a laser device and an electronic video dental camera. The teachings of this invention overcome the disadvantages of prior art dental laser instruments which do not provide for other than direct viewing of the treatment area by the dentist, as well as the disadvantages of attempting to use such prior art dental laser instruments together with typical prior art viewing devices such as denetal mirrors and dental cameras of the prior art. The dental instrument includes a laser device and an electronic video dental camera is provided having a single handle and a convenient shape, thereby being readily manipulated by dentists who are universally familiar with the manipulation of prior art dental tools. The dental instrument includes a handle to be held by the user, a distal portion which is to be placed inside the patient's mouth, a laser light emission port located at or near the distal end, means for transporting laser light from an external laser source to the laser light emission port, and a camera head located at or near the distal end of the device, with the camera head being formed in order to provide a field of view which includes the portion of the patient which is being treated by the laser light emanating from the laser light emission port.

30 Claims, 8 Drawing Sheets

U.S. PATENT DOCUMENTS

| | | | |
|---|---|---|---|
| 4,369,768 | 1/1983 | Vukovic | 128/6 |
| 4,385,344 | 5/1983 | Gonser | 362/804 |
| 4,390,028 | 6/1983 | Okano . | |
| 4,402,326 | 9/1983 | Okano . | |
| 4,425,599 | 1/1984 | Rieder . | |
| 4,457,502 | 7/1984 | Beach . | |
| 4,468,197 | 8/1984 | Provost | 433/30 |
| 4,475,539 | 10/1984 | Konomura . | |
| 4,479,499 | 10/1984 | Alfano | 433/29 |
| 4,491,865 | 1/1985 | Danna . | |
| 4,492,574 | 1/1985 | Warrin . | |
| 4,503,853 | 3/1985 | Ota . | |
| 4,516,195 | 5/1985 | Gonser . | |
| 4,522,196 | 6/1985 | Cunningham et al. | 128/4 |
| 4,539,586 | 9/1985 | Danna . | |
| 4,568,283 | 2/1986 | Hotta . | |
| 4,575,805 | 3/1986 | Moermann et al. | 433/55 |
| 4,593,699 | 6/1986 | Poncy | 128/662.03 |
| 4,601,284 | 7/1986 | Arakawa et al. | 128/6 |
| 4,608,622 | 8/1986 | Gonser . | |
| 4,621,618 | 11/1986 | Omagari | 128/6 |
| 4,629,425 | 12/1986 | Detsch | 433/31 |
| 4,638,353 | 1/1987 | Nagasaki et al. | 358/98 |
| 4,667,229 | 5/1987 | Cooper et al. | 358/98 |
| 4,684,018 | 8/1987 | Jarund | 206/306 |
| 4,727,416 | 2/1988 | Cooper | 358/229 |
| 4,744,752 | 5/1988 | Nakayama . | |
| 4,747,661 | 5/1988 | Ohkuwa . | |
| 4,757,381 | 7/1988 | Cooper | 433/29 |
| 4,759,347 | 7/1988 | Ando | 128/6 |
| 4,761,719 | 8/1988 | Yamada . | |
| 4,804,329 | 2/1989 | Nakayama . | |
| 4,820,152 | 4/1989 | Warrin . | |
| 4,826,431 | 5/1989 | Fujimura | 433/29 |
| 4,836,782 | 6/1989 | Gonser . | |
| 4,849,859 | 7/1989 | Nagasawa . | |
| 4,850,868 | 7/1989 | Wright . | |
| 4,858,001 | 8/1989 | Milbank | 128/6 |
| 4,915,626 | 4/1990 | Lemmey | 433/29 |
| 4,940,411 | 7/1990 | Vassiliadis | 433/29 |

OTHER PUBLICATIONS

Incipient Caries," *The Journal of Prosthetic Dentistry* (1985) 53:776–777.

Fact Sheet on the American Dental Laser by American Dental Laser Incorporated of Birmingham, Michigan.

Survey of Patients Treated with the American Dental Laser by American Dental Laser Incorporated of Birmingham, Michigan.

Benefits of the American Dental Laser for the Dentist by American Dental Laser Incorporated of Birmingham, Michigan.

Case Studies of Procedures with an American Dental Laser by American Dental Laser Incorporated of Birmingham, Michigan.

The Revolutionary American Dental Laser of Birmingham, Michigan.

"A short introduction to low level laser therapy," by Creative Medical Systems, Ltd. of the Netherlands.

Myers, "Dental Technology: Knocking at High-Tech's Door," *The Journal of the American Dental Association* (1989) 118:285–294.

Myers et al., "In vitro caries removal," *CDA Journal* (1988), pp. 9–10.

Myers et al., "First Soft Tissue Study Utilizing a Pulsed Nd; YAG Dental Laser," *Northwest Dentistry* (1989), pp. 14–16.

Myers et al., "What Lasers Can Do for Dentistry and You," *Dental Management* (1989) 29:26–30.

Dunlap, "Is There a Laser in Your Future," *Dental Economics* (1989).

*Laser Magazine,* NR. 1, Aug. (1989) Various articles and authors.

DENTAL INSTRUMENT INCLUDING LASER DEVICE AND ELECTRONIC VIDEO DENTAL CAMERA

RELATED APPLICATIONS

This is a continuation-in-part of U.S. Ser. No. 149,521, filed 1/29/86, now abandoned, which is a continuation-in-part of U.S. Ser. No. 022,171, filed 3/5/87 which has now issued as U.S. Pat. No. 4,727,416, and which are both assigned to Fuji Optical Systems, Inc.

FIELD OF THE INVENTION

This invention pertains to a dental instrument, and more specifically to a dental instrument including a laser device integrally formed with an electronic video dental camera.

BACKGROUND

For years, dentists have used dental mirrors for insertion in a dental patients' mouth for reflecting images of areas within the patients' mouth for viewing by the dentist. This technique works, although it has several disadvantages. First, it is often difficult to hold the dental mirror in an appropriate position in order to reflect the desired image. Secondly, it is more difficult to ensure that proper lighting is available to the area within the mouth to be reflected by the dental mirror. An even greater disadvantage is that it is very difficult to use such prior art dental mirrors in a situation where a dentist wishes to discuss certain regions within the mouth with other people, be it the patient, colleagues, dental assistants, or students in a teaching institution.

Electronic video endoscopes have been used in recent years, for example as is described in U.S. Pat. application Ser. No. 611,684 filed May 18, 1984 on an invention of Cooper et al, which is hereby incorporated by reference. Such prior art video endoscopes use either fiber optics or a miniature camera, such as a charge coupled device (CCD), in order to transport an image to a monitor. Such prior art video endoscopes come in a variety of sizes, but are typically rather small and tubular in nature in order that they maybe easily inserted within a body cavity or surgical opening. Certain prior art endoscopes include a light source located at their end in order to ensure proper lighting is available for illumination of the area of the desired image.

However, such prior art video endoscopes were not specifically designed for use in dental applications and are rather clumsy in such applications. As one example, it is very difficult, if not impossible, to properly view the lingual aspects of the teeth using such prior art video endoscopes, due to their tubular shape.

A number of attempts have been made in the prior art to provide intraoral camera devices. Such attempts are illustrated in U.S. Pat. Nos. 3,382,781; 4,468,197; 4,479,499; 4,629,425, European Patent Application No. 0 122 537 A; Offenlegunsgsschrift 2,208,902: and Offenlegunsgsschrift DE 304 5162 Al.

It is also known in the prior art to use lasers in conjunction with dental procedures, as described, for example, in Myers, "Dental Technology: Knocking at High-Tech's Door," *The Journal of the American Dental Association* (1989) 118:285-294; Myers, "A Review of Lasers in Dentistry," *Il Dentista Moderno* (1989); Myers, "In vitro caries removal," *CDA Journal* (1989) pp. 9-10; Myers et al., "First Soft Tissue Study Utilizing a Pulsed Nd:YAG Dental Laser," *Northwest Dentistry* (1989) pp. 14-16; Myers et al., "The Use of a laser for Debridement of incipient caries," *The Journal of Prosthetic Dentistry* (1985) 53:776-777; Myers et al., "What Lasers Can Do for Dentistry and You," *Dental Management* (1989) 29:26-30; Dunlap, "Is There A Laser In Your Future," *Dental Economics* (1988); *Laser Magazine,* NR. 1, August (1989) (Various articles and authors).

However, such prior art laser dental instruments require the dentist performing the procedure to rely on viewing the treatment area directly or via an independent mirror. Direct viewing is often awkward and does not provide the dentist with an adequate visual acuity or sufficient clarity to accurately and efficiently perform the procedure. The use of prior art viewing tools, such as a standard dental mirror or even prior art dental imaging devices, used in conjunction with a prior art dental laser instrument, is awkward at best, and in most instances, simply impractical. Furthermore, laser energy is dangerous to the patient if not applied properly, and is dangerous to the dentist and his assistant if the laser energy is accidentally reflected by a mirror, particularly if the reflected laser energy reaches their eyes.

Thus there remains the need to provide a dental practitioner with improved visual acuity, sufficient clarity, and an appropriate field of view when performing laser procedures in a convenient and confident manner, while providing a safe working environment for the patient, the practitioner, and bystanders.

SUMMARY OF THE INVENTION

In accordance with the teachings of this invention, a novel dental instrument is taught which includes both a laser device and an electronic video dental camera. The teachings of this invention overcome the disadvantages of prior art dental laser instruments which do not provide for other than direct viewing of the treatment area by the dentist, as well as the disadvantages of attempting to use such prior art dental laser instruments together with typical prior art viewing devices such as dental mirrors and dental cameras of the prior art. In accordance with the teachings of this invention, a dental instrument including a laser device and an electronic video dental camera is provided having a single handle and a convenient shape, thereby being readily manipulated by dentists who are universally familiar with the manipulation of prior art dental tools. A dental instrument constructed in accordance with the teachings of this invention includes a handle to be held by the user, a distal portion which is to be placed inside the patient's mouth, a laser light emission port located at or near the distal end, means for transporting laser light from an external laser source to the laser light emission port, and a camera head located at or near the distal end of the device, with the camera head being formed at an angle to the handle in order to provide a field of view which includes the portion of the patient which is being treated by the laser light emanating from the laser light emission port.

In one embodiment, means are provided to cause, as desired, the flow of a selected fluid or gas over the camera lens in order to defog and/or clean the camera lens, thereby allowing proper viewing. In one embodiment, the camera head also includes light sources for properly illuminating the area to be viewed. As a feature of one embodiment of this invention, the handle of the dental camera includes means for communicating all appropriate signals and fluids to and from the camera head and the laser light emission port, and, if desired, valves and switching means located on the handle for controlling such communication.

DETAILED DESCRIPTION OF THE INVENTION

In accordance with the teachings of this invention, a novel dental instrument is provided which allows the dental practitioner to direct laser energy to a desired location within a patient's mouth. The dental instrument of this invention also includes means for providing a video image of the area to which the laser energy is directed for viewing on a video screen, recording on a video tape recorder providing photographs, and the like. By providing a dental instrument which not only allows laser energy to be directed to a desired location within the patient's mouth but also which provides a magnified view on a video screen of the operative area, the dental practitioner is afforded significantly improved imaging which enables the practitioner to perform the procedure with a high degree of confidence that the laser energy is directed to the desired area, and only the desired area, within the patient's mouth, thereby making the procedure quicker, more effective, and safer. By providing a single dental instrument which is used for both directing the laser energy and providing a view of the operative area, the practitioner can perform the procedure with far greater ease than when utilizing both a laser instrument and a dental mirror for viewing purposes.

Figure 1:
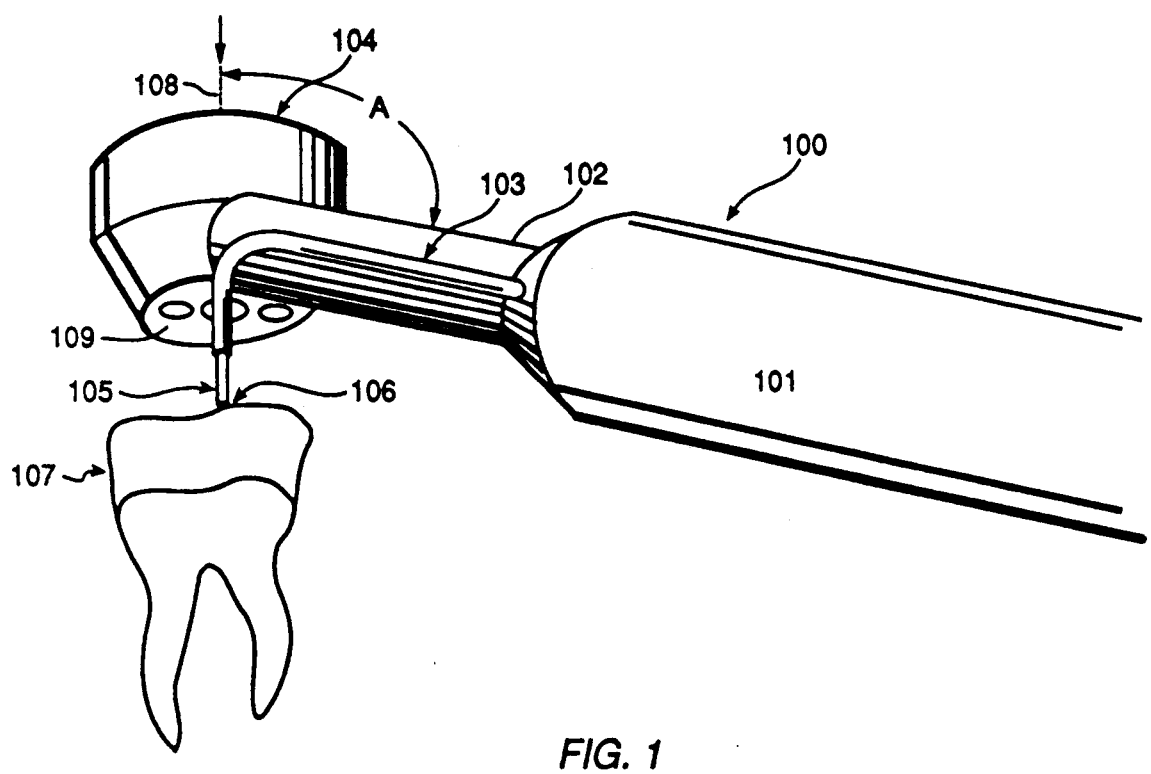
FIG. 1 is an external view of one embodiment of a dental instrument constructed in accordance with the teachings of this invention.

FIG. 1 shows a view of one embodiment of a dental instrument constructed in accordance with the teachings of this invention. Dental instrument 100 includes handle 101 suitable for being held by an operator, and, if desired having forward extension or neck 102. At the proximal end (not shown) of handle 101 is located one or more connectors for connection, via a cable assembly (not shown) to a video processor and control unit and a source of laser energy. Preferably, means for providing illumination to the treatment area is included. The light source can be located in head 104, or away from head 104 (for example in neck 102, handle 101, or in the video processor and control unit) and communicated to the treatment area by optical fiber, for example. In one embodiment of this invention, video processor and control unit comprise the EVE system processor available from Fuji Optical Systems, Inc. of Los Gatos, California. If desired, color images can be obtained as described in "Ultracompact CCD Color Television Camera", Takemura et al., Toshiba Review No. 158 Winter (1986), pp. 3-6, and U.S. Pat. Nos. 4,727,416 and 4,667,229, assigned to Fuji Optical Systems, Inc., the assignee of this application.

In one embodiment of this invention, the laser source comprises, for example, a typical prior art YAG laser capable of providing sufficient power to the treatment area. Preferably, the laser source is capable of providing laser light to the treatment area over a wide range of power levels, pulse repetition rates, and pulse widths. Also, preferably the laser source includes a means for providing not only infrared energy from a YAG laser, for example, but also visible light from any suitable source, which is carefully aligned with the infrared laser energy in order to serve as a visible targeting or aiming beam to insure that the operator is aware of where the infrared energy is being directed.

If desired, neck 102 and handle 101 have generally circular cross section, although suitable shapes, such as octagonol, oval, and polygonal can be used. The important point is that handle 101 is easily and comfortably gripped by the user, and neck 102 is of a general size and cross section which is convenient for insertion into the patient's mouth and, of course, comfortable for the patient.

Located at the distal end of neck 102 and mounted on neck 102 at an angle A to neck 102, is camera head 104. Face 109 of camera head 104 includes means for receiving an image within a patient's mouth to be displayed on a video monitor. In one embodiment of this invention, such means for receiving the image is fiber optic tubes or one or more rod or relay lens assemblies or a combination thereof with or without additional lenses, which transmit the image to an image sensor (not shown) either within neck 102 or handle 101. In another embodiment of this invention, the image is transmitted by one or more rod or relay lens assemblies or fiber optic cable, or a combination thereof with or without additional lenses, through a connector (not shown) at the proximal end of handle 101 to an image sensor located in handle 101 or in external video equipment (not shown). However, in a preferred embodiment the image sensor is located directly in camera head 104 and receives the image from the patient's mouth via a lens, without the need for fiber optics. By utilizing a video monitor, magnification of the image of the dental procedure is provided, thereby enabling the dentist to more easily and accurately perform a procedure. For example, when utilizing a monitor having a 13 inch screen (diagonal measure), magnification of approximately 18X is provided. Convenient and well framed video recording of laser dental procedures are also now possible utilizing this invention.

Of importance, the field of view provided by the means for receiving an image contained in camera head 104 is designed to encompass that area where the laser dental procedure is being performed, i.e. in the case of FIG. 1 the field of view is the portion of tooth 107 where the laser energy is directed, as well as a reasonable area surrounding that point, and may include either the entire tooth, several teeth, or, if desired, even a full arch. For example, the field of view is typically within the range of approximately 5 to 50 mm in order to allow the dentist to view not only the specific point at which the laser energy is directed, but surrounding areas of the tooth. In accordance to the teachings of this invention, the field of view appears highly magnified on a video screen, thereby allowing the laser energy to be directed with great accuracy, confidence, and safety.

Also shown in FIG. 1 is means for transmitting laser energy 103 from a laser source (not shown) to the area being treated. In one embodiment of this invention, means for transmitting laser energy 103 comprises a fiber optic member 105, preferably a single optical fiber constructed of glass, quartz, or other suitable material, capable of handling the power and wavelength of the laser energy being provided. In the embodiment of FIG. 1, fiber optic member 105 is protected over much of its length by conduit 103, which is located external to neck 102. In an alternative embodiment of this invention, fiber optic member 105 is formed within neck 102, obviating the need for additional protective conduit 103. Conduit 103 may be used as a guide to place optical fiber 105 at the point of interest.

As shown in the embodiment of FIG. 1, the laser energy is emitted from fiber optic member 105 such that the maximum energy density occurs at the end of fiber optic member 105, with the laser energy rapidly dispersing with increasing distance from the end of fiber optic member 105. In this manner, the dental instrument of FIG. 1 serves as a contact device, i.e. when the end of fiber optic member 105 is brought in close contact with an object, such as a tooth or gum, the laser energy is of sufficient density to perform the dental procedure. However, as the end of fiber optic member 105 is moved away from a surface, the laser light emanating is dispersed such that the energy density at any particular point is significantly reduced, thereby preventing the laser energy from having an effect on other than a particular small area, as desired. It has been determined that such a contact device can be provided simply by allowing the laser energy to emanate from the end of fiber optic member 105. This causes the maximum energy density of the laser light to be essentially at the termination of the optical fiber, providing a contact device.

Figure 2:
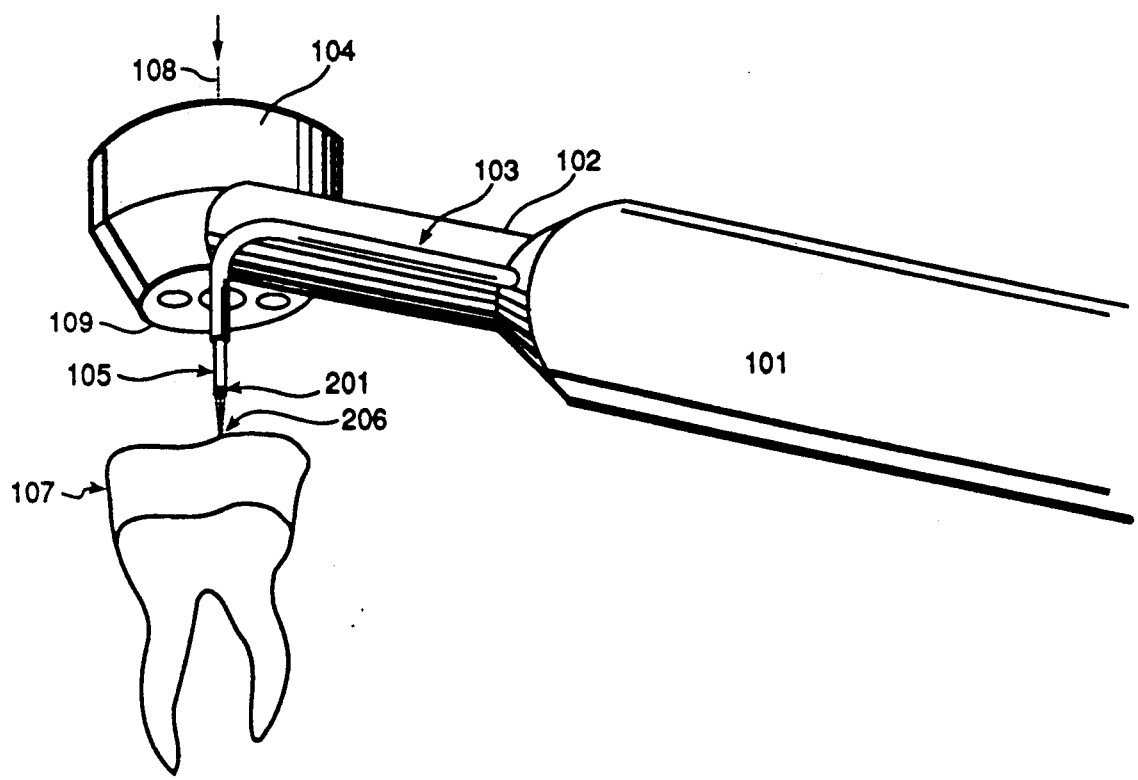
FIG. 2 is an external view of another embodiment of a dental instrument constructed in accordance with the teachings of this invention.

Alternatively, it is possible to provide a lens at the end of laser energy transmission means 105 so that the focal point is at a distance from the lens, thereby providing a non-contact device. FIG. 2 is a view of such an alternative embodiment of this invention in which the instrument is a non-contact device. In this embodiment, means is provided to insure that the laser energy emanating from fiber optic member 105 has a focal point at a predefined distance from the end of fiber optic member 105. In one embodiment of this invention, focusing lens 201 is applied to the end of optical fiber member 105 in order to provide a desired focal length. Such a focal length can be of any desired dimension and is typically within the range of approximately 0 to 50 mm.

In one embodiment of this invention, a noncontact device is provided which includes means for providing a visible light signal to the area where the operative laser energy is directed or to be directed, thereby serving as an aiming beam. In one embodiment, this visible light is provided by a visible laser, such as a laser diode providing visible light, a HeNe laser, or a non-laser light source. Of importance, the focal point of the visible light target beam is substantially the same as the focal point of the operative laser beam, thereby allowing easy and precise aiming of the operative laser beam. In one embodiment of this invention, switch means, such as a foot switch which is easily manipulated by the dentist is provided for turning on the operative laser energy. When the operative laser energy is not engaged, the visible light signal is engaged in order to allow the dentist to properly align the dental instrument of this invention prior to causing the operative laser beam to be engaged. If desired, the visible light beam can either remain engaged or be turned off when the operative laser energy is turned on.

In one embodiment of this invention an infrared blocking filter is placed in the image path between the image being viewed and the image sensor (not shown) in order to prevent infrared energy from being applied to the image sensor. If not blocked out, the infrared energy from the laser would be detected by the image sensor, resulting in a "washed out" video signal.

In accordance with the teachings of this invention, a number of possible adapter lenses are provided, included but not limited to a wide angle lens, a telephoto lens, a rod lens, a relay lens, or one or more fiber optic cables serving as a "relay lens". Such a telephoto adapter lens is very convenient for viewing very small areas, for example for use in viewing the capillaries within the gums, thereby allowing the dentist or oral surgeon to determine the relative health of the gums by determining the condition of blood circulation within the gums, which is useful, for example, when performing gingevectomy. Such a telephoto adapter lens is also useful for obtaining a frontal view of the entire mouth, by holding the telephoto adapter lens at an appropriate distance from the patient's face. Use of a telephoto adapter lens for this purpose provides a more highly magnified image and avoids the frontal image of the patient's mouth appearing as a "fish eye" view. A tiny relay adapter lens is highly suitable for viewing the small spaces between the teeth more readily than can be viewed using the dental camera itself.

Figure 3A:
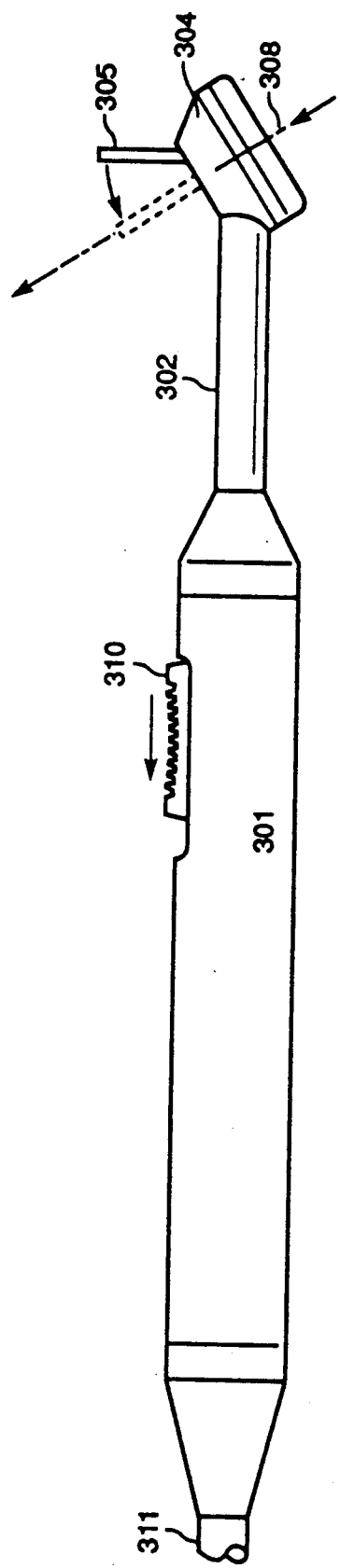
FIGS. 3a and 3b are external views of another embodiment of a dental instrument constructed in accordance with the teachings of this invention which include a flexible light probe.
Figure 3B:
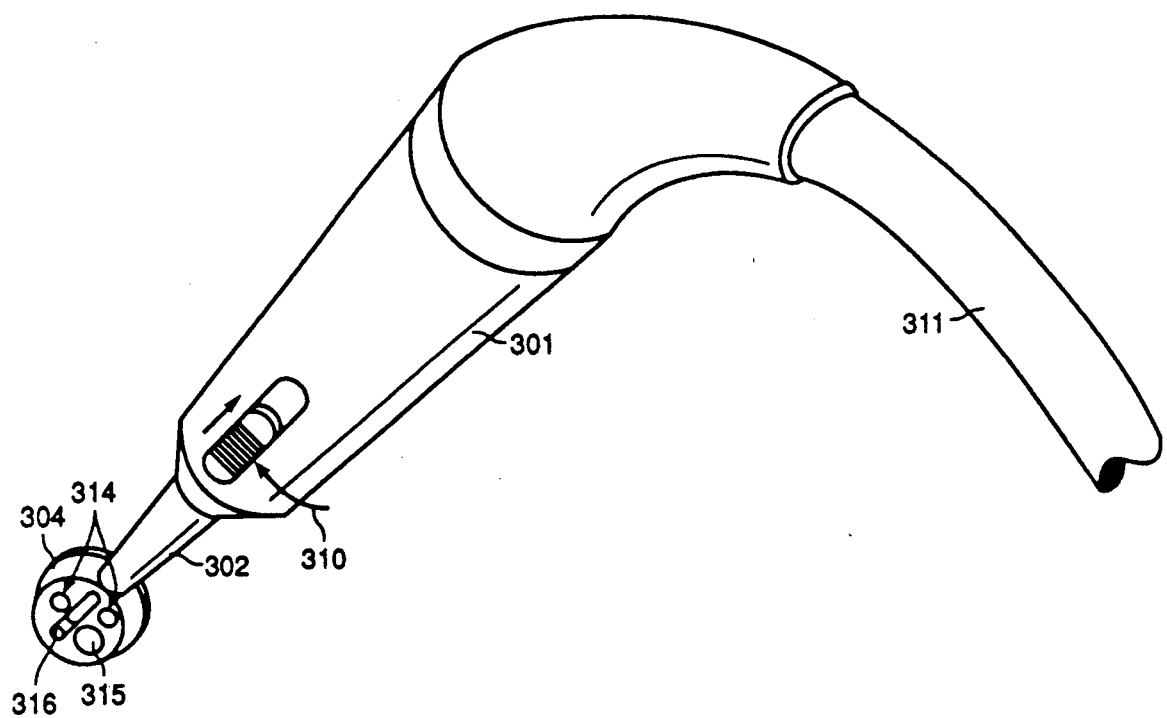

FIGS. 3a and 3b depict an alternative embodiment of this invention which includes a flexible light probe 305 emanating from camera head 304. In one embodiment, flexible light probe 305 is conveniently fabricated as the distal end of, or an extension of, fiber optic member 105 (FIG. 1). Flexible light probe 305 is capable of being manipulated to alter its exit angle from camera head 304, and thus alter viewing axis 308. Also shown in FIGS. 3a and 3b is light probe elevator control 310 which is located on handle 301 for easy manipulation by the practitioner in order to move flexible light probe 305 as desired. This allows the practitioner to hold the instrument in a convenient position and alter slightly the target area which will receive the laser energy, thereby making use of the dental instrument constructed in accordance with the teachings of this invention more convenient than if the target area cannot be altered with respect the position of the dental instrument. Also shown in FIGS. 3a and 3b are cable assembly 311, camera lens 315, illuminating lenses 314, and channel opening 316 through which flexible light probe protrudes. While the embodiments of FIGS. 3a and 3b depict the elevator control located on handle 301 of the dental instrument, in alternative embodiments the elevator control is located elsewhere.

Figure 4:
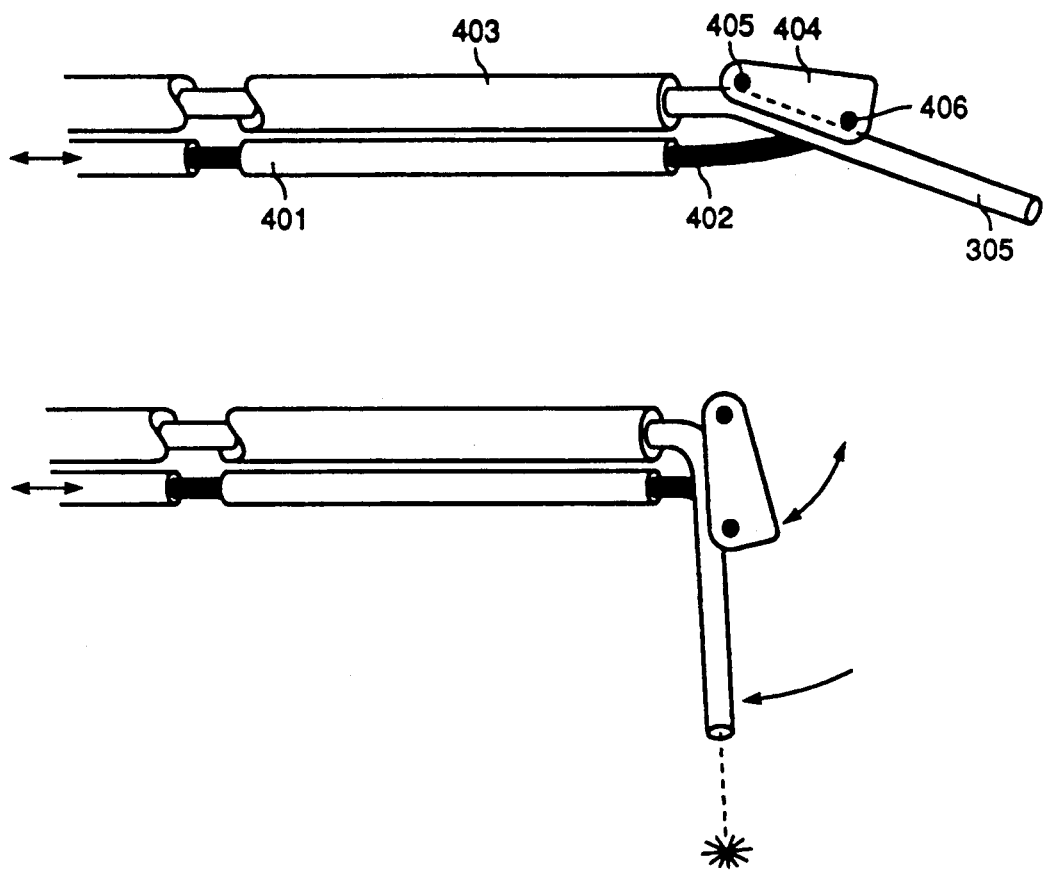
FIG. 4 is a view depicting an elevator assembly for manipulating the flexible light probe of FIGS. 3a and 3b.

FIG. 4 depicts one embodiment of an elevator assembly constructed in accordance with the teachings of this invention to allow flexible light probe 305 of FIG. 3a to be easily manipulated. As shown in FIG. 4, flexible light probe 305 is an extension of an optical fiber which is held by optical fiber guide channel 403. Elevator 404 pivots about pivot point 405 in order to cause angular displacement of light probe 305. Elevator 404 pivots in response to movement of elevator wire 402 which is tied to elevator 404 at tie point 406. Elevator wire 402 is contained within wire guide channel 401 in a well known fashion and is actuated by light probe elevator control 310 of FIGS. 3a and 3b. It is to be understood that the embodiment of FIG. 4 is but one mechanism for manipulating light probe 305 and may be housed within the dental instrument of FIGS. 3a and 3b or may be conveniently housed external to such a dental instrument, as desired.

It is contemplated by this invention that this elevator technique can also be used to easily manipulate items other than, or in addition to, light probe 305. For example, this technique and structure can be used to manipulate a washing tube, for example, which serves to provide a fluid or gas jet in order to cleanse an area where a dental procedure is being performed.

Figure 5A:
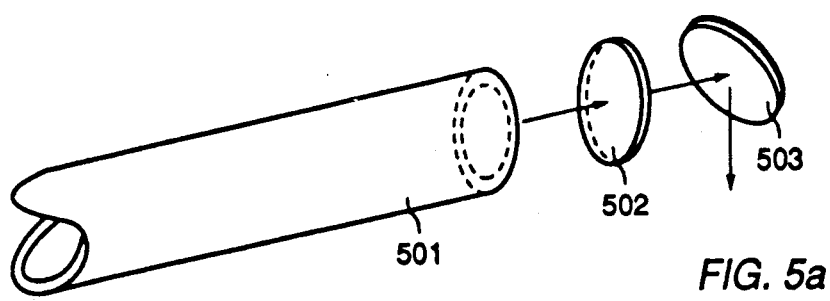
FIGS. 5a through 5e depict various embodiments of this invention which allows light to exit a fiber optic light guide at an angle which is substantially perpendicular to the longitudinal axis of the light guide.

In an alternative embodiment of this invention, a dental instrument is provided in which the fiber optic member need not be bent about a sharp radius, thereby making manufacture simpler and more cost effective. As shown in FIG. 5a, attached to the distal end of optical fiber 501 is lens 502 and mirror 503. Mirror 503 serves to reflect the laser energy to a desired angle from the longitudinal axis of optical fiber 501, with the angle of redirection being any desired angle, although an angle within the range of approximately 40 to 135 degrees is often useful.

Figure 5B:
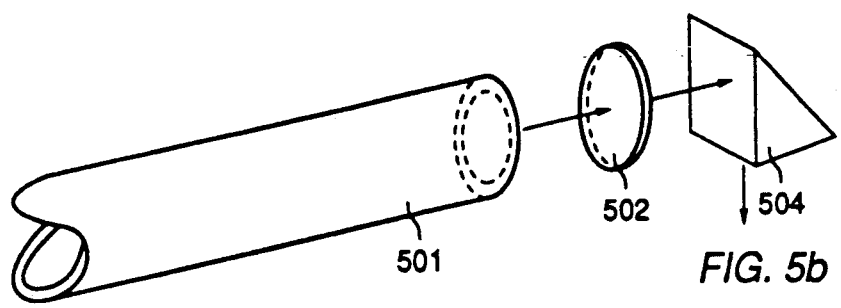

In FIG. 5b, an alternative embodiment is shown, including prism 504 used in place of mirror 503 of FIG. 5a.

Figure 5C:
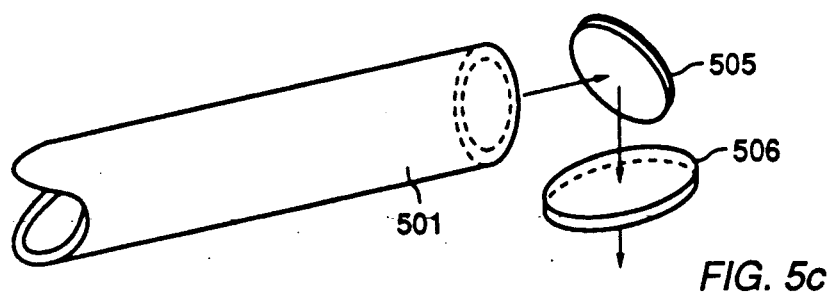

FIG. 5c shows an alternative embodiment where mirror 505 is placed between optical fiber 501 and lens 506.

Figure 5D:
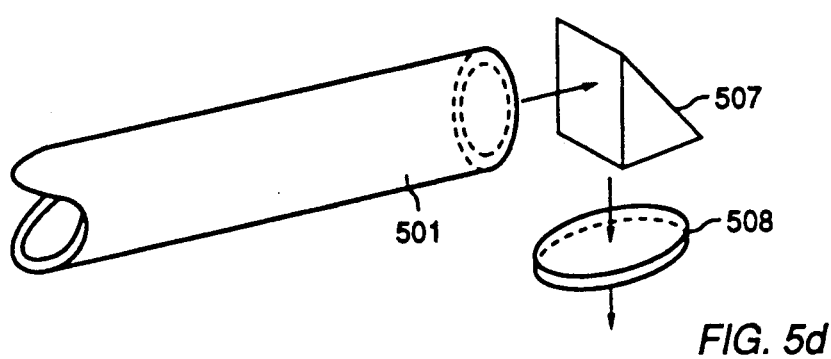

FIG. 5d shows an alternative embodiment where prism 507 is placed between optical fiber 501 and lens 508.

Figure 5E:
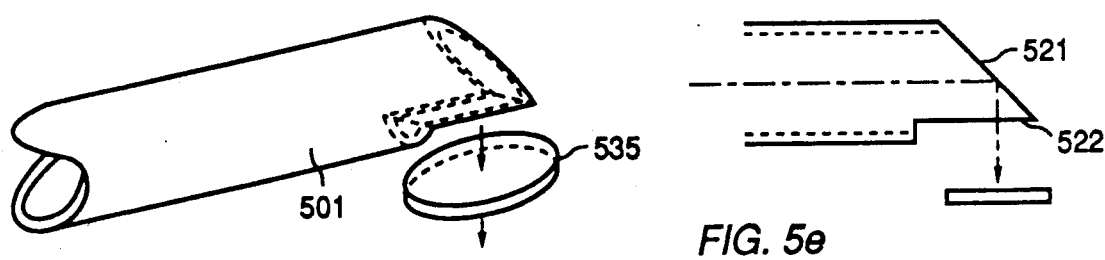

FIG. 5e shows yet another embodiment in which a mirror is formed integrally with optical fiber 501 by forming the distal end of optical fiber 501 at an angle to the longitudinal axis of optical fiber 501, thereby providing mirror surface 521. A portion of the outer surface of optical fiber 501 is removed to form a notch which serves as exit port 522, allowing the light reflected from mirror surface 521 to exit from optical fiber 501 at an angle to the longitudinal axis of optical fiber 501. If desired, mirror surface 521 is polished and, preferably, coated in order to form a highly reflective mirror surface. If desired, lens 535 is used to focus the light exiting optical fiber 501 at exit port 522. Lens 535, if used, may either be attached to optical fiber 501 at exit port 522, or may be mounted at a desired distance from exit port 522.

Figure 6:
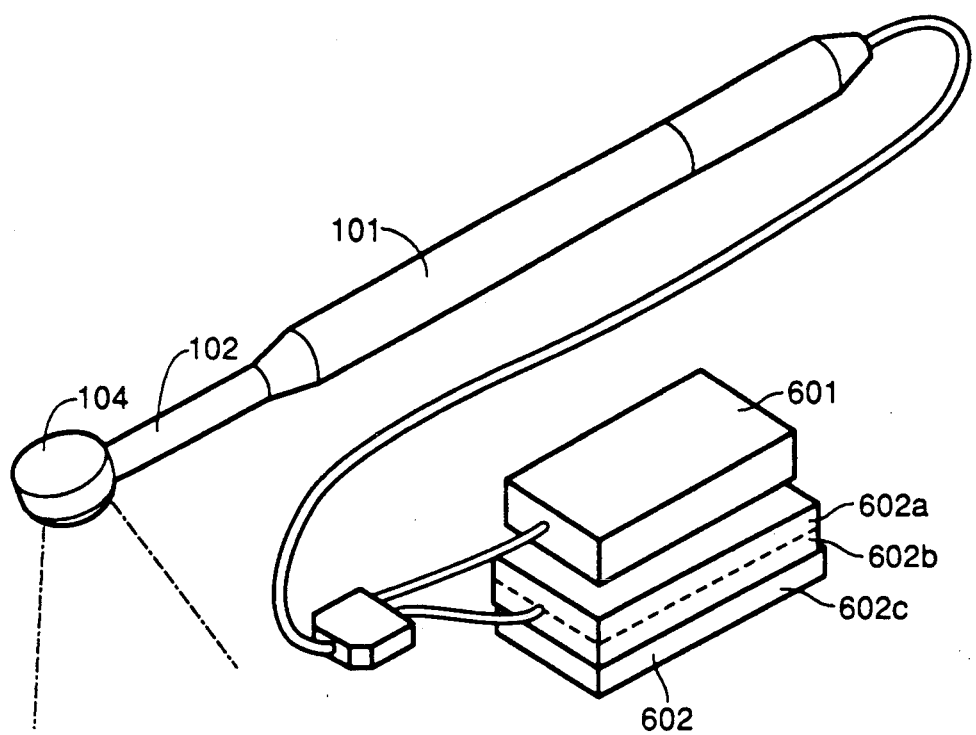
FIG. 6 is a diagram depicting one embodiment of this invention including a camera located external to the handle, and an illumination light source, a laser light source, and an aiming beam light source.

FIG. 6 is a diagram depicting one embodiment of this invention in which camera 601 is located external to handle 101, neck 102, and head 104. Light source 602 includes illumination light source 602a, laser light source 602b, and aiming beam light source 602c.

Figure 7:
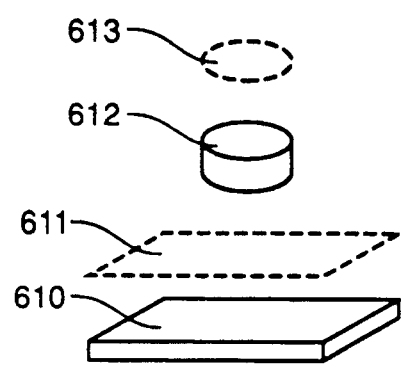
FIG. 7 depicts one embodiment of the camera of FIG. 6.

FIG. 7 depicts one embodiment of camera 601 of FIG. 6. As shown in FIG. 7, camera 601 includes image device (such as a CCD) 610, lens 612, and one or more filters 611, 613. Such lenses may include an infrared light filter.

Figure 8:
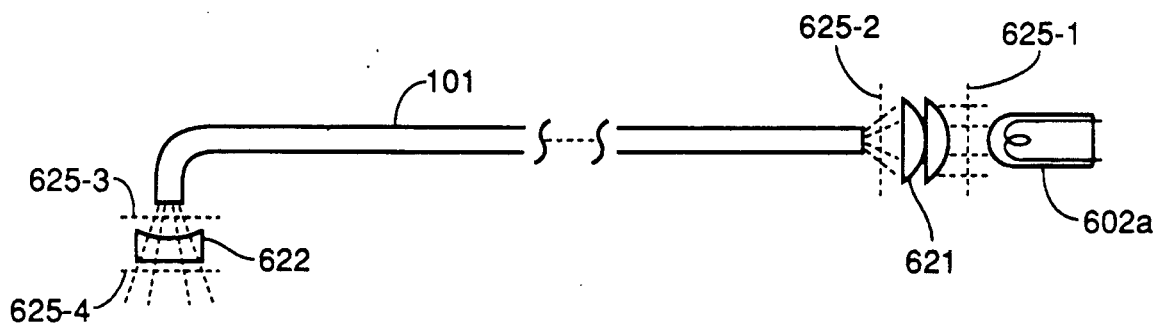
FIG. 8 depicts one embodiment of the illumination feature of this invention.

FIG. 8 depicts one embodiment of a device constructed in accordance with this invention including illumination light source 602a, lenses 621 and 622, and the illumination light path within handle 101. Various locations 625-1 through 625-4 are shown for the placement of one or more filters within the path of the illumination beam.

All publications and patent applications are herein incorporated by reference to the same extent as if each individual publication or patent application was specifically and individually indicated to be incorporated by reference. The invention now being fully described, it will be apparent to one of ordinary skill in the art that many changes and modifications can be made thereto without departing from the spirit or scope of the appended claims.

What is claimed is:

1. A dental instrument for use in displaying an image from inside the mouth onto a monitor comprising an electronic video endoscope comprising:
    a handle;
    means for emitting laser energy, located at the distal end of said handle; and
    a camera head located at the distal end of said handle including a means for receiving an image, such that said image includes the area of the mouth to which said laser energy is directed.

2. A dental instrument as in claim 1 wherein said laser energy comprises infrared energy.

3. A dental instrument as in claim 1 wherein said laser energy comprises infrared energy plus visible light directed along the same path as said infrared energy.

4. A dental instrument as in claim 1 wherein said means for emitting laser energy is such that the maximum energy density of said laser energy is located substantially at the point said laser energy exits said means for emitting laser energy.

5. A dental instrument as in claim 1 wherein said means for receiving an image is selected from the group of mirrors, lenses, optical fibers, and filters.

6. A dental instrument as in claim 1 which further comprises means for transmitting said image from said camera head to an imaging device located external to said dental instrument.

7. A dental instrument as in claim 1 wherein said means for receiving an image is placed at an angle from the axis of said handle.

8. A dental instrument as in claim 1 wherein said means for emitting laser energy comprises means for emitting laser energy which is focused at a preselected distance from said distal end of said handle.

9. A dental instrument as in claim 8 wherein said preselected distance is within the range of approximately 0 to 50 mm.

10. A dental instrument as in claim 1 which further comprises:
    a light probe through which said laser energy emanates; and
    means for controlling said light probe in order to direct the laser energy along a desired path with respect to said dental instrument.

11. A dental instrument as in claim 10 wherein said light probe comprises an optical fiber.

12. A dental instrument as in claim 10 which further comprises an elevator control for controlling said light probe.

13. A dental instrument as in claim 1 wherein said camera head includes an image device and electronic circuitry including one or more drivers for controlling said image device or amplifiers for amplifying signals received from said image device.

14. A dental instrument as in claim 13 which further comprises a filter located in the path of said image.

15. A dental instrument as in claim 14 wherein said filter is located between said means for receiving an image and said image device.

16. A dental instrument as in claim 14 wherein said filter is an infrared blocking filter.

17. A dental instrument as in claim 1 which further comprises a camera lens which is removably connected to said camera head.

18. A dental instrument as in claim 17 wherein said camera lens is selected from the group of camera lenses consisting of wide angle, telephoto, rod, relay, and fiber optic lenses.

19. A dental instrument as in claim 17 wherein said camera lens comprises an additional means for providing light toward the area being viewed by said camera head.

20. A dental instrument as in claim 19 which further comprises a filter in the path of the light from said light source.

21. A dental instrument as in claim 1 which further comprises:
    an image device; and
    means for transmitting said image from said camera head to said imaging device.

22. A dental instrument as in claim 21 wherein said imaging device is located in said camera head.

23. A dental instrument as in claim 21 wherein said imaging device is located in said handle.

24. A dental instrument as in claim 21 wherein said imaging device is located external to said camera head and external to said handle.

25. A dental instrument as in claim 1 which further comprises a light probe for directing said laser energy along a desired path with respect to said dental instrument, said light probe comprising:
    an optical fiber; and
    means for directing said laser energy along a desired light path.

26. A dental instrument as in claim 25 wherein said means for directing comprises a mirror or a prism.

27. A dental instrument as in claim 25 wherein said means for directing comprises the distal end of said optical fiber which is cut at an angle to the longitudinal axis of said optical fiber; and
    a notch cut along the outer surface of said optical fiber at its distal end to serve as a point of exit of said laser light from said optical fiber.

28. A dental instrument as in claim 27 wherein said distal end of said optical fiber is polished and/or coated.

29. A dental instrument as in claim 27 which further comprises a lens attached to said notch.

30. A dental instrument as in claim 27 which further comprises a lens which is not attached to said notch.

* * * * *